United States Patent [19]

Fehr et al.

[11] Patent Number: 5,585,535
[45] Date of Patent: Dec. 17, 1996

[54] SOYBEANS AND SOYBEAN PRODUCTS HAVING LOW PALMITIC ACID CONTENT

[75] Inventors: Walter R. Fehr; Earl G. Hammond, both of Ames, Iowa

[73] Assignee: Iowa State University Research Foundation, Inc., Ames, Iowa

[21] Appl. No.: 376,470

[22] Filed: Jan. 20, 1995

Related U.S. Application Data

[63] Continuation of Ser. No. 180,112, Jan. 12, 1994, abandoned, which is a continuation of Ser. No. 839,329, Feb. 20, 1992, abandoned, which is a continuation-in-part of Ser. No. 461,361, Jan. 5, 1990, abandoned.

[51] Int. Cl.⁶ .............................. A01H 5/00; A01H 5/10; C12N 15/01
[52] U.S. Cl. .................. 800/200; 800/230; 800/250; 800/DIG. 26; 800/DIG. 69; 435/172.1; 426/601
[58] Field of Search .................... 800/200, 230, 800/250, DIG. 26, DIG. 69; 426/601; 435/172.1

[56] References Cited

U.S. PATENT DOCUMENTS 4,948,811  8/1990  Spinner et al. ..................... 514/560

OTHER PUBLICATIONS

Kuhr et al 1987 Release Notice for N85–2124, N85–2131, and N85–2176.
Carter et al 1988 Release Notice for C1726 and C1727.
Wilson 1987 In Soybeans: Improvement, Production and Uses; Agronomy Monograph No. 16; Wilcox (ed) pp. 643, 662–686.
Mounts et al 1987 In Soybeans: Improvement, Production and Uses; Agronomy Monograph No. 16; Wilson (ed) pp. 819–845, 860–865.
Weihrauch et al 1977 Food Technology 31: 80–85 and 91.
Wilcox et al 1984 J Am Oil Chem Soc 61:97–100.
Wilson et al 1981 Crop Sci 21: 788–791.
Burton et al 1983 Crop Sci 23: 744–747.
Erickson et al 1988 Crop Sci 28: 644–646.
Bubeck et al 1989 (May–Jun.) Crop Sci 29: 652–656.
Wilson et al (1987 J Am Oil Chem Soc 64:1262 (Abstract P–5).
Wilcox 1989 (5 Mar.) World Soybean Res Conf IV pp. 28–39.
USDA and N.C. Agric. Res. Service Release Notice for Soybean N79–2077–12, dated Aug. 1990.

*Primary Examiner*—Patricia R. Moody
*Attorney, Agent, or Firm*—Burns, Doane, Swecker & Mathis, L.L.P.

[57] ABSTRACT

A method is described for producing soybean varieties and lines exhibiting low palmitic acid contents of less than about 6.0% of the total fatty acid composition down to no more than about 2.4% or lower. The novel soybean lines are obtained by crossing C1726 and A1973NMU-173 and by utilizing selected progeny from such crossing. Soybean lines having stearic acid contents of less than about 3.0%, down to about 1.5% and total saturated fatty acid contents less than about 7.0% down to no more than about 4.0% are also disclosed.

14 Claims, No Drawings

SOYBEANS AND SOYBEAN PRODUCTS HAVING LOW PALMITIC ACID CONTENT

This is a continuation of application Ser. No. 08/180,112 filed 12 Jan. 1994 (now abandoned), which is a continuation of Ser. No. 07/839,329 filed 20 Feb. 1992 (now abandoned), which is a continuation-in-part of Ser. No. 07/461,361 filed 5 Jan. 1990 (now abandoned).

FIELD OF THE INVENTION

This invention relates to novel soybean seeds and products of soybean seeds, such as soybean oil, and, more particularly, to soybean seeds and products containing a low level of saturated fatty acids, specifically low levels of palmitic acid.

BACKGROUND OF THE INVENTION

Soybeans represent a significant world-wide food source, providing an excellent source of protein. As such, soybeans represent a potential alternative to meats.

Tofu and soymilk are two principal food products derived from soybean seeds. More than one billion people in China and Southeast Asia, it has been stated, rely on tofu as a major food protein source. (Proc. Int. Soya Protein Food Conf., American Soybean Assoc., p. 35, 1978). Soymilk is similarly an important source for food protein.

Soybean seeds also represent perhaps the most significant oilseed in the world and contain significant nutritive properties. Soybean oil has thus been considered to be the major vegetable oil produced and consumed in the United States, and more than 90% of this soybean oil is used in food products (World Soybean Research Conference III Proceeding, Shibles, R. (Ed.), 1985).

Soybeans contain two different saturated fatty acids, viz.—palmitic acid (16:0) and stearic acid (18:0). Palmitic acid is generally the major constituent, comprising some 70% of the total saturated fatty acid content.

The presence of the more typical level of palmitic acid may be considered undesirable for some applications. Extending back to the 1950's, the medical community has emphasized the role of fat intake in the pathogenesis of heart disease. The American Heart Association issued a series of reports dating from 1957 to the present; each report emphasized alteration of the diet by reducing intake of saturated fats. The Association has continued to recommend such a reduction and currently suggests that saturated fats comprise no more than 10% of the total calories of an individual's intake.

This is particularly true of saturated fatty acids having a chain length of 12 to 16, which includes palmitic acid. There is some evidence that stearic acid, having a chain length of 18, is less injurious or even perhaps beneficial with respect to artery disease.

A major competitor of soybeans for the vegetable oil market is canola. Canola has been promoted as a healthier oil than soybean oil because of its relatively lower saturated fatty acid content. It would be a significant advance to be able to provide soybean oil which would have a palmitic acid content similar to that of canola.

The formidable nature of the task to provide a saturated acid content in soybeans similar to that in canola can be appreciated from a recent report wherein it was stated that palmitic acid levels in soybean seed oil range from 9.3% to 17.4% within the world collection (Erickson et al., *Journal of Heredity*, 79, p. 465, 1988). The level of palmitic acid would have to be reduced substantially below the reported minimum of 9.3% to provide a palmitic acid content similar to that of canola. Thus, the palmitic acid content of canola would be expected to be below about 6%; and applicants are aware of reported palmitic acid levels down to about 4% or even slightly less.

The Erickson et al. article reports the inheritance of altered palmitic acid percentage in two soybean mutants, C1726 and C1727. The level of palmitic acid in C1726 averages 8.5%, and the range of values obtained is set forth. The lines resulting from crossing the mutant line C1726 with the commercial cultivar "Century" a re, also described.

It may also be desirable for some applications to develop a soybean line characterized by a low stearic acid content or a soybean line characterized by a low total saturated fatty acid content.

Despite the clear need for soybeans having a significantly reduced level of palmitic acid, this objective still remains to be achieved.

SUMMARY OF THE INVENTION

It has been discovered that crossing two particular mutants, C1726 and A1937NMU-173, provides a population of soybean seeds exhibiting significantly reduced levels of palmitic acid. The palmitic acid concentration obtained is less than about 6.0%, preferably less than 5.5%, more preferably less than about 4.5%, and even more preferably less than about 4.0% of the total fatty acid present. Palmitic acid contents down to about 3.5% have been obtained.

In accordance with this invention, it has also been discovered that utilizing selected progeny can provide soybean lines having palmitic acid contents of no more than about 2.5% or even less. Further, soybean lines may be provided that are characterized by stearic acid contents of less than about 3.0%, preferably no more than about 2.0%, and/or total saturated fatty acid contents of no more than about 7.0%, preferably no more than about 5.0%, and, more preferably, no more than about 4.0%.

If desired, the soybeans of the present invention can be used as a donor parent in a backcrossing program with any desired commercial cultivar as a recurrent patent to isolate a variety having desirable seed yield and other agronomic characteristics, in addition to the reduced level of palmitic acid.

DETAILED DESCRIPTION OF PREFERRED EMBODIMENT

The novel soybean seeds and plants of the present invention, characterized by reduced levels of palmitic acid, were obtained by crossing mutant lines C1726 and Asgrow A1937NMU-173. C1726 is a mutant line developed and released by The United States Department of Agriculture (Agricultural Research Service) and the Purdue University Agricultural Experiment Station. According to the developers, the line C1726 averages 8.5% palmitic acid and was originated as an $M_2$ plant from a population of Century soybean treated with ethyl methane sulfonate.

The line A1937NMU-173 was selected from the progeny of a population developed by treatment of seeds of the cultivar Asgrow A1937 with nitroso methyl urea (NMU). The mutation procedure utilized will be described in detail hereinafter.

Crossing of the parent mutant lines C1726 and A1937NMU-173 to obtain the soybean line of the present invention can be carried out by any desired hybrid formation technique. Standard hybridization techniques are, of course, well known and may be utilized. As an illustrative example, hybridization techniques are disclosed in Fehr, *Principles of Cultivar Development*, Vol. 1, Theory and Technique, Chapter 13, pp. 156–164, Macmillan Publishing Company, New York, 1987, which hybridization techniques are herein incorporated by reference.

Progeny from the crossing of C1726 and A1937NMU-173 include soybean seeds wherein the palmitic acid content is less than 6.0% of the total fatty acid composition, preferably less than about 5.5%, more preferably, less than about 4.5%, and even more preferably less than about 4.0%. Surprisingly, soybean lines having as low as about 3.5% palmitic acid were obtained.

The fatty acid composition was determined by gas-liquid chromatography using the method as generally outlined in Graef et al. (*Crop. Sci.,* 25: 1076–1079, 1985). Thus, in general, the method comprises (1) crushing the seed sample, (2) putting the crushed sample into a test tube with a hexane solvent and extracting the oil into the hexane, (3) the fatty acids in the oil are converted to their methyl esters using sodium methoxide and methanol, (4) water is added to inactivate the sodium methoxide catalyst, and (5) the methyl esters, which float to the top of the water layer, are diluted with hexane and become the sample that is introduced into the column of the gas chromatography apparatus.

As may be appreciated, this general methodology may be employed and specific aspects changed to lessen the time needed as desired. For example, the stationary phase selected for the columns will dictate the temperature at which the sample can be introduced.

None of the specifics utilized, e.g.—capillary versus packed columns, are considered to affect to any appreciable extent the results obtained for an analysis. Rather, such specifics affect the time required for sample preparation and analysis.

The percentages of the fatty acids set forth herein, unless otherwise designated, thus are on a weight basis and refer to the percentage of the methyl ester of palmitic acid or other fatty acid compared to the total methyl esters of the fatty acid composition in the sample being analyzed. This can also be taken as the weight percentage of the fatty acid itself because the difference between the palmitic acid content and that of its methyl ester as determined in the gas chromatography technique described herein is so minimal as may be ignored, as is commonly done in this field.

The gas chromatography techniques described herein are routinely used for analysis of the fatty acid composition of soybeans. The experimental error is considered to be within the range of from about 1 to 5% or so, depending upon the magnitude of the peak. For example, with a relatively large peak indicative of an oleic acid content of 50% or so, the experimental error may be as low as about 1% of the value, viz.—50±0.5%. At the other extreme, a small peak indicative of a palmitic acid content of 4.0% may have an experimental error of about 5.0% of the value, viz.—4.0%±0.2.

As may be appreciated, the palmitic acid levels of the soybeans of the present invention set forth herein were obtained from soybeans grown in Iowa and Puerto Rico. Growth under climatic conditions cooler or warmer may result in a somewhat altered fatty acid composition. However, while the specific results may vary somewhat depending upon the specific growing conditions experienced, the progeny of the present invention will be characterized by extremely low palmitic acid contents relative to other soybean lines grown under similar conditions.

Progeny exhibiting the desired low palmitic acid trait can be crossed with other progeny to provide a population of soybean seeds having extremely low palmitic acid contents. It is theoretically possible that the methodology disclosed in the present invention may be utilized to yield soybean seeds, products and oil with down to zero palmitic acid. It can be expected that crosses utilizing the more desirable progeny should be capable of providing lines having palmitic acid contents down to about 3.0% or 2.5%, or even down to about 2.0% or so.

Indeed, in accordance with the present invention, crosses utilizing the more desirable progeny have already provided soybean lines characterized by palmitic acid contents down to 2.4%. As will be described in the Examples, crossing of progeny from the crossing of C1726 and A1937NMU-173 with the commercial cultivar Kenwood result in soybean lines having such extremely low palmitic acid contents.

Pursuant to a further aspect of this invention, soybean lines are provided that are characterized by stearic acid contents of less than 3.0%, preferably less than 2.0%, and, more preferably, no more than about 1.5%. Additionally, soybean lines are provided that have total saturated fatty acid contents of less than 7.0%, preferably less than 5.0%, and, more preferably, no more than about 4.0%.

These low stearic acid content and/or low total saturated fatty acid content soybean lines may likewise be obtained by using selected progeny from the low palmitic acid soybean lines disclosed herein. To this end, such low stearic acid content and/or low total saturated fatty acid content soybean lines can be obtained by crossing the commercial cultivar Kenwood with selected progeny from the crossing of C1726 and A1937NMU-173. A particularly desirable progeny in this respect is AX5152-105.

It can be expected the crosses utilizing the more desirable progeny should be capable of providing soybean lines having stearic acid contents down to about 1.0% or so. Similarly, utilizing the more desirable progeny should be capable of providing soybean lines having total saturated fatty acid contents down to about 3.0% or so.

Further, progeny can be crossed, if desired, with other progeny, or with any other soybean line or cultivar to yield a soybean cultivar having the desired seed yield or other desired agronomic traits as well as the desired low palmitic acid trait. Self-pollination of selected progeny may likewise yield lines having characteristics desired for some applications.

Any hybridization technique may be used, and many are known as has been described herein. For example, the selection of progeny having the desired low palmitic acid trait can be obtained by conducting recurring backcrossing with a commercial variety until a desirable variety has been isolated. Backcrossing techniques are known, as disclosed in Fehr, *Principles of Cultivar Development,* Vol. 1, Theory and Technique, Chapter 28, pp. 360–376, the disclosure of which is herein incorporated by reference.

As one example, backcrossing using the desired $F_2$ seeds obtained by natural self-pollination of the $F_1$ plants could be carried out as follows:

(1) Plant $F_1$ seeds obtained by crossing a parent with the desired low palmitic acid trait to the desired commercial cultivar (recurrent parent). Sample $F_2$ seeds from $F_1$ plants are analyzed for fatty acid concentration, and seeds with the desired low palmitic acid content are planted for backcrossing.

(2) Cross-pollinate the desired commercial cultivar (recurrent parent) with an $F_2$ plant having the low palmitic acid content.

(3) Plant the $BC_1F_1$ seeds and obtain $BC_1F_2$ seeds by natural self-pollination. Sample $BC_1F_2$ seeds are analyzed for fatty acid concentration, and those displaying the low palmitic acid trait are backcrossed to the recurrent parent.

(4) The backcross and selection procedure herein described (Step 3) can be repeated until lines with the desired low palmitic acid composition and agronomic performance are recovered. It is believed that four of these backcross cycles should serve to transfer the low palmitic acid trait to the desired cultivar (viz.—recurrent parent), although the number of such cycles can be fewer, or more, as is desired. The result is the production of a soybean line quite similar to the commercial cultivar except having the desired low palmitic acid content.

Any commercial cultivar (recurrent parent) desired may be employed for backcrossing. Factors such as, for example, seed yield, geographical area, and many others, as is known, will generally dictate the cultivar selected from the several hundred commercial cultivars available.

The following Examples are illustrative, but not in limitation, of the present invention. The gas chromatography results obtained from the instrument itself are reported to two decimal points (i.e.—"0.00"). As reported herein, the fatty acid values are set forth to one decimal point. Values of 6 or more in the second decimal point were raised (e.g.—4.29 is reported herein as 4.3), values of 4 or less are ignored (e.g.—4.24 is reported as 4.2), values of 5 are raised if the first decimal is odd (e.g.—4.15 is reported as 4.2) and ignored if even (e.g.—4.25 is reported as 4.2).

EXAMPLE 1

This Example describes the preparation of the mutant line A1937NMU-173.

Mutant line A1937NMU-173 was obtained from nitroso methyl urea (NMU) treatment of the parent variety Asgrow A1937. In May, 1985, 2,500 seeds of A1937 were soaked in 2.5 L distilled water in a 6 L flask for 9 hours at room temperature. The flask was aerated for the 9 hours of soaking. The water was drained from the flask, and 2.5 L of 2.5 mM NMU in 0.1 molar phosphate buffer at pH 5.5 were added. The seeds were soaked with aeration for 3 hours, the solution was drained and the seeds were rinsed twice with distilled water. Treated seeds were placed in plastic bags to prevent drying and transported to the Agricultural Engineering and Agronomy Research Center near Ames, Iowa. The seeds were planted 2.5 cm deep in moist soil within 4 hours after the last rinse. The soil was watered regularly to keep it moist until seeding emergence. The properties of the mutant seed and their progeny were evaluated beginning with the $M_4$ generation.

A similar number of seeds was harvested from each of the $M_1$ (first mutant generation) plants in the population to obtain 2,000 $M_2$ seeds. A random sample of 1,000 of the second generation $M_2$ seeds from the population was planted in October at the Iowa State University-University of Puerto Rico soybean nursery at Isabela, Puerto Rico. About 2,000 $M_3$ seeds were obtained by harvesting a similar number of seeds from each $M_2$ plant. In February, 1,000 $M_3$ seeds were planted in Puerto Rico. About 2,000 $M_4$ seeds were obtained by harvesting a similar number of seeds from each $M_3$ plant.

In May, 1,000 $M_4$ seeds were planted at Ames. Five hundred $M_4$ plants were harvested individually from the population, and a 10-seed sample from selected plants was analyzed by gas-liquid chromatography to determine the fatty acid composition. $M_5$ progeny of selected plants were planted in Puerto Rico in November, 1987; and the results confirmed the unique fatty acid composition of the $M_4$ parent plant.

Table I sets forth the analysis of the fatty acid composition of a 10-seed sample from the $M_4$ plant from which A1937NMU-173 originated as well as that of its parent:

TABLE I

| Seed Identification | Fatty Acid Composition | | | | |
| --- | --- | --- | --- | --- | --- |
| | Palmitic Acid (16:0) | Stearic Acid (18:0) | Oleic Acid (18:1) | Linoleic Acid (18:2) | Linolenic Acid (18:3) |
| A1937NMU-173 | 6.8 | 2.8 | 19.7 | 61.4 | 9.3 |
| A1937 parent | 12.3 | 3.8 | 18.7 | 57.2 | 8.0 |

Table II sets forth the analysis of $M_5$ progeny from the $M_4$ plant A1937NMU-173 as well as that of A5, a line with a palmitic acid content considered to be typical of commercial soybean varieties:

TABLE II

| Seed Identification | Fatty Acid Composition | | | | |
| --- | --- | --- | --- | --- | --- |
| | Palmitic Acid (16:0) | Stearic Acid (18:0) | Oleic Acid (18:1) | Linoleic Acid (18:2) | Linolenic Acid (18:3) |
| A1937NMU-173 | 7.2 | 3.6 | 21.3 | 59.2 | 8.7 |
| A5 | 10.5 | 3.9 | 29.6 | 51.7 | 4.3 |

EXAMPLE 2

This Example describes the crossing of C1726 and A1937NMU-173 to obtain the soybean lines of the present invention characterized by low palmitic acid contents.

Reciprocal crosses were made between C1726 and A1937NMU-173 at the Agricultural Engineering and Agronomy Research Center near Ames, Iowa, during the summer of 1988. The hybrid $F_1$ seeds obtained from the cross were designated AX5152.

The $F_1$ and parent seeds were split so that the embryo was left intact. The non-embryo portion (approximately one-third of the seed) was analyzed for fatty acid composition. The seed portion containing the embryo of each $F_1$ and parent seed was planted in the Iowa State University-University of Puerto Rico nursery at Isabela, Puerto Rico, in October, 1988. $F_2$ seeds were obtained by natural self-pollination. Each $F_1$ and parent plant was harvested individually.

Ten $F_2$ seeds from each of the $F_1$ plants designated AX5152-7, AX5152-34, AX5152-105, AX5152-115, and AX5152-123 were split; and the nonembryo portion of the $F_2$ seeds was analyzed for fatty acid composition by gas chromatography. The embryo portion of each of these seeds was planted at the Agronomy Research Center near Ames, Iowa, in May, 1989. Eleven individual F3 seeds were analyzed from each $F_2$ plant.

Table III summarizes the analysis of the fatty acid composition of the $F_2$ seeds from Puerto Rico having the desired low palmitic acid content and that of the parent lines:

TABLE III

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| C1726 Parent[1] | 8.2 | 3.8 | 21.5 | 58.6 | 7.9 |
| A1937NMU-173 Parent[2] | 7.8 | 4.4 | 19.4 | 59.8 | 8.5 |
| AX5152-7 | 4.3 | 4.3 | 24.8 | 59.1 | 7.4 |
| AX5152-34 | 4.8 | 3.5 | 21.2 | 61.6 | 8.9 |
| AX5152-105 | 5.5 | 3.1 | 19.7 | 63.2 | 8.5 |
| AX5152-115 | 3.6 | 3.4 | 24.4 | 62.0 | 6.6 |
| AX5152-123 | 4.4 | 3.5 | 21.0 | 63.0 | 8.1 |

[1]Average of 9 seeds, palmitic acid contents ranged from 8.0 to 8.3% among the individual seeds.
[2]Average of 10 seeds, palmitic acid contents ranged from 7.4 to 8.3% among the individual seeds Table VI summarizes the analysis of the fatty acid composition of the $F_3$ progeny from the $F_2$ plants as well as that of the parents:

TABLE IV

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| C1726 Parent | 8.1 | 3.4 | 25.2 | 55.1 | 8.3 |
| A1937NMU-173 Parent | 6.9 | 3.8 | 28.1 | 53.8 | 7.4 |
| AX5152-7 | 4.2 | 3.3 | 24.7 | 59.7 | 8.0 |
| AX5152-34 | 4.6 | 3.0 | 31.4 | 53.5 | 7.4 |
| AX5152-105 | 4.6 | 2.7 | 22.3 | 61.0 | 9.4 |
| AX5152-115 | 4.2 | 3.4 | 25.7 | 59.3 | 7.3 |
| AX5152-123 | 4.4 | 2.7 | 39.3 | 47.4 | 6.2 |

EXAMPLE 3

This Example describes the crossing of AX5152-105, obtained as described in Example 2, with the commercial cultivar Kenwood to obtain soybean lines of the present invention characterized by low stearic acid and low total saturated fatty acid contents.

Crosses were made between the cultivar Kenwood and AX5152-105 at the Iowa State University-University of Puerto Rico nursery during March 1990. The hybrid $F_1$ seeds obtained from the cross were designated AX7343.

$F_1$ plants of the cross AX7343 were grown at the Agricultural Engineering and Agronomy Research Center near Ames, Iowa, during the summer of 1990. $F_2$ seeds were obtained by natural self-pollination. A total of 1,000 $F_2$ seeds from the cross were planted in November, 1990, in the Iowa State University-University of Puerto Rico nursery at Isabela, Puerto Rico. $F_3$ seeds were obtained by natural self-pollination. Three seeds were harvested from each $F_2$ plant to obtain a bulk sample of $F_3$ seeds from the population. A random sample of 870 $F_3$ seeds was planted in Puerto Rico in February, 1991. $F_4$ seeds were obtained by natural self-pollination. Three $F_4$ seeds were harvested from each $F_3$ plant to obtain a bulk sample of $F_4$ seeds from the population. In May, 1991, a random sample of the 1050 $F_4$ seeds was planted at the Agricultural Engineering and Agronomy Research Center near Ames, Iowa. Approximately 845 $F_4$ plants were harvested individually, and a 10-seed sample from each plant was analyzed by gas-liquid chromatography to determine fatty acid composition.

Table V sets forth the fatty acid composition of the $F_4$ plant characterized by a low palmitic acid content, a low stearic acid content and a low total saturated fatty acid content, as well as the fatty acid composition of the parent lines:

TABLE V

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX7343-25 | 2.5 | 1.9 | 24.9 | 57.9 | 12.8 |
| Kenwood | 12.1 | 4.3 | 21.3 | 55.2 | 7.1 |
| AX5152-105 | 3.7 | 3.1 | 19.8 | 64.5 | 9.0 |

Twenty-four $F_5$ seeds of the plant AX7343-25 were split so that the embryonic axis was left intact. The portion of each seed without the embryonic axis (approximately one-third of the seed) was analyzed for fatty acid composition by gas chromatography.

Table VI sets forth the fatty acid composition of individual $F_5$ seeds characterized by the lowest palmitic acid content, lowest stearic acid content, and the lowest total saturated fatty acid content ever reported for soybeans as far as applicants are aware, as well as the fatty acid compositions of the parent lines:

TABLE VI

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX7343-25-19 | 2.4 | 1.8 | 24.2 | 59.8 | 11.8 |
| AX7343-25-23 | 2.5 | 1.5 | 24.1 | 58.3 | 13.6 |
| Kenwood | 12.5 | 4.3 | 22.4 | 53.6 | 7.2 |
| AX5152-105 | 3.9 | 3.2 | 21.8 | 62.7 | 8.4 |

2,500 seeds of A1937NMU-173 were deposited on Jan. 26, 1996 under the Budapest Treaty in the American Type Culture Collection (ATCC) at 12301 Parklawn Drive, Rockville, Md. 20852, U.S.A., and have been assigned ATCC Accession No. 97429. Additionally, 2,500 seeds of C1726 have been deposited under the Budapest Treaty at the same depository on the same date and have been assigned ATCC Accession No. 97430.

Although the foregoing invention has been described in detail with examples for purposes of understanding the invention, it will be understood by those skilled in the art that various modifications of the invention may be practiced while remaining within the spirit and the scope of the appended claims.

What is claimed is:

1. A method for producing a soybean plant that yields mature seed having a reduced endogenous palmitic acid content comprising:
   (a) crossing a first soybean parent plant that is C1726 having ATCC Accession No. 97430, with a second soybean parent plant that is A1937NMU-173 having ATCC Accession No. 97429;
   (b) obtaining hybrid soybean seeds from the cross and germinating said seeds to produce segregating populations of soybean plants that are allowed to self-pollinate; and
   (c) selecting a plant of step (b) that yields mature seed following self pollination having an endogenous palmitic acid content in the oil thereof in an amount lower than the palmitic acid of the parent plant of step (a) having the lower endogenous palmitic acid content when the parent plants and the offspring of the cross are grown under the same conditions.

2. A method according to claim 1 wherein said soybean plant that is selected in step (c) contains an endogenous palmitic acid content in the oil of the mature seed formed thereon of less than about 6% by weight as determined by gas chromatography.

3. A method according to claim 1 wherein said soybean plant that is selected in step (c) contains an endogenous palmitic acid content in the oil of the mature seed formed thereon of less than about 5.5% by weight as determined by gas chromatography.

4. A method according to claim 1 wherein said soybean plant that is selected in step (c) contains an endogenous palmitic acid content in the oil of the mature seed formed thereon of less than about 4.5% by weight as determined by gas chromatography.

5. A method according to claim 1 wherein said soybean plant that is selected in step (c) contains an endogenous palmitic acid content in the oil of the mature seed formed thereon of less than about 4% by weight as determined by gas chromatography.

6. A method according to claim 1 wherein said soybean plant that is selected in step (c) contains an endogenous palmitic acid content in the oil of the mature seed formed thereon from about 2.4% to about 5.5% by weight as determined by gas chromatography.

7. A soybean plant which upon self pollination yields mature seed that exhibits a reduced palmitic acid content and is the product of crossing a first soybean parent that is C1726 having ATCC Accession No. 97430, with a second soybean parent that is A1937NMU-173 having ATCC Accession No. 97429, and wherein the soybean plant resulting from said cross yields mature seed that provides an endogenous oil comprising palmitic acid in an amount lower than the endogenous palmitic acid content of the parent having the lower palmitic acid content when the parent plants and the offspring of said cross are grown under the same conditions.

8. A mature soybean seed formed by the self pollination of the soybean plant according to claim 7, and the descendants thereof that retain said reduced palmitic acid content when grown under the same conditions.

9. A mature soybean seed formed by the self pollination of the plant selected in step (c) of the method of claim 1 and descendants thereof which upon self pollination forms mature seeds that retain said reduced palmitic acid content when grown under the same conditions.

10. A mature soybean seed according to claim 8 that contains an endogenous palmitic acid content of less than about 6% by weight as determined by gas chromatography.

11. A mature soybean seed according to claim 8 that contains an endogenous palmitic acid content of less than about 5.5% by weight as determined by gas chromatography.

12. A mature soybean seed according to claim 8 that contains an endogenous palmitic acid content of less than about 4.5% by weight as determined by gas chromatography.

13. A mature soybean seed according to claim 8 that contains an endogenous palmitic acid content of less than about 4% by weight as determined by gas chromatography.

14. A mature soybean seed according to claim 8 that contains an endogenous palmitic acid content from about 2.4% to about 5.5% by weight as determined by gas chromatography.

\* \* \* \* \*